United States Patent
Yu et al.

(12)

(10) Patent No.: US 6,262,172 B1
(45) Date of Patent: Jul. 17, 2001

(54) METHOD FOR PREPARING A CARBONIZED RESIN DNA IMMUNOADSORBENT

(75) Inventors: Yaoting Yu; Changzhi Chen; Deling Kong, all of Tianjin (CH)

(73) Assignee: Nankai University (CN)

( * ) Notice: Subject to any disclaimer, the term of this patent is extended or adjusted under 35 U.S.C. 154(b) by 0 days.

(21) Appl. No.: 09/499,312

(22) Filed: Feb. 7, 2000

(30) Foreign Application Priority Data

Jun. 8, 1998 (CH) ................................................ 98102355

(51) Int. Cl.[7] .......................... C08G 64/48; C08G 63/91; C07C 2/00
(52) U.S. Cl. ..................... 525/54.2; 521/134; 585/500; 585/507; 585/832; 525/54.2; 525/50
(58) Field of Search ............................ 521/134; 585/500, 585/507, 832; 525/54.2, 50

(56) References Cited

FOREIGN PATENT DOCUMENTS 0272792    6/1988   (EP) .

OTHER PUBLICATIONS

Terman, David S. et al., "Extracorporeal Immunoadsorption: Initial Experience in Human Systemic Lupus Erythematosus"; The Lancet, Oct. 20, 1979, pp. 824–826.

*Primary Examiner*—Jezia Riley
(74) *Attorney, Agent, or Firm*—Burns, Doane, Swecker & Mathis, L.L.P.

(57) ABSTRACT

A method for preparing a carbonized resin DNA immunoadsorbent, which uses styrene, acrylonitrile, divinylbenzene, toluene, liquid paraffin, benzoyl peroxide and water solution of polyvinyl alcohol as raw materials, produces a DNA immunoadsorbent with 0.3–0.5 mg DNA per milliliter of resin using two-staged procedures for preparation of first carbonized resin, and secondly carbonized resin DNA immunoadsorbent. The resultant immunoadsorbent is high in adsorbent capacity, low in production cost, and can be synthesized without pyrogens. It therefore satisfies the demands of medical application for the treatment of systemic lupus erythematosus by immunoadsorption.

2 Claims, No Drawings

METHOD FOR PREPARING A CARBONIZED RESIN DNA IMMUNOADSORBENT

This application claims priority under 35 U.S.C. §§119 to 98102355.X filed in People's Republic of China on Jun. 8, 1998, the entire contents of which are hereby incorporated by reference.

FIELD OF THE INVENTION

This invention relates to clinically useful material, and in particular to an immunoadsorbent resin prepared by immobilizing biologically active DNA to a carbonized resin as a carrier, adapted for hemoperfusion for the treatment of systemic lupus erythematosus (SLE).

BACKGROUND OF THE INVENTION

Systemic lupus erythematosus is an autoimmune disease. Its etiology is still under investigation and currently there is no effective treatment. Mortality is usually caused by multiple organ failure in SLE patients, and the death rate is fairly high.

Utilization of extracorporeal immunoadsorbent to treat SLE was first introduced in 1987. This was described in the patent of Jnes, Frank R., EP 0 272 792 A1 (1987). The hemoperfusion in STE therapy with DNA immunoadsorbent utilizes the specificity of the immobilized DNA on the stationary resin to remove the disease-causing anti-DNA antibody in the circulating blood of SLE patients, thereby reversing the clinical symptoms, and improving the immune function of the SLE patients, allowing them to recover gradually. This treatment method is attracting increasing attention in clinical medicine.

Terman D. S. et al reported the first usage in extracorporeal immunoadsorption by DNA immobilized by enclosure with collodion membrane adsorbed to active charcoal to treat a 29-year-old woman with severe lupus nephritis (Lancet, 1979, 2(8147):824–827). Her life span was extended by 31 days by the hemoperfusion. This opened up a new research era of SLE therapy. However, because Terman employed active charcoal as carrier, the mechanical strength and resilience of the adsorbent were poor, with shedding of fine charcoal particles that would clog the blood capillaries.

Yang Y. et al employed carbonized resin from Japan as carrier for the collodion membrane-enclosed DNA adsorbent, where the DNA was pretreated by blue tetrazolium (Chinese Journal of Biomedical Engineering, 1985, 4(2):88–95, Chemical Journal of Chinese Universities, 1985, 6(9):843–847). This immunoadsorbent showed greatly enhanced mechanical strength, and lack of shedding of the immobilized DNA. It was used successfully for the clinical treatment of SLE patients in China with evident therapeutic effects. However, the presence of endotoxin was indicated by patients' shivering. In addition, improvement in the enclosure method is required in order to increase the adsorbent function. Furthermore, there is need to improve the method of preparation of the carbonized resin, and lowering its cost, in order to advance the clinical application of the adsorbent.

SUMMARY OF INVENTION

Because the structure and function of the resin carrier and its compatibility with blood directly affect the clinical utilization of the DNA immunoadsorbent resin, the present invention describes an improved method of preparing a carbonized resin DNA immunoadsorbent. The present invention improves the DNA enclosure procedure, enhances the immunoadsorption function, and makes possible the ready avoidance the introduction of pyrogens, in order to increase clinical effectiveness. The production cost of the material is also substantially reduced.

In this invention, the DNA immunoadsorbent uses carbonized resin as carrier for immobilizing an effective amount of DNA. The DNA content attains the level of 0.3–0.5 mg/ml resin. Briefly, the two-staged preparation steps are:

(a) Preparation of carbonized resin

Styrene and acrylonitrile were used as monomers, divinylbenzene as crosslinker, toluene and liquid paraffin (equivalent to three times by weight the total monomers and crosslinker) as porogens, benzoyl peroxide as initiator, and 1–2% of polyvinyl alcohol as dispersing agent. Polymerization was carried out at 80° C. for 5 hours. Toluene was distilled off at 96° C. The globular polymer was heated at 100° C. for 2–3 hours for further polymerization and hardening, washed with hot water, and heat dried at 50° C. Petroleum ether was applied to remove the paraffin. The result was a tri-component macroporous resin.

The resin was placed in a resistance oven, and under the protection with inert gas, heated to 100–300° C. in an oven for 8–10 hours. The temperature was then further increased to 500–800° C. Steam was introduced to activate the resin for 0.5–1.0 hour. The desired carbonized resin was obtained after cooling.

(b) Preparation of carbonized resin DNA immunoadsorbent

Calf thymus DNA was uniformly mixed with collodion. Under vigorous stirring, the carbonized resin was added and the liquid was absorbed quickly. The reaction mixture was stirred intermittently and washed for 2 hours at 50–60° C. in a water bath until the solvent was totally evaporated. The resin was vacuum dried at 50° C. for 2 hours, and washed several times with water. After packing into a column, the resin was washed further until the eluent was devoid of absorbance at 260 nm. The resin was further washed again and dried with suction at 50° C. to yield the immunoadsorbent.

The carbonized resin DNA immunoadsorbent prepared by this method contained 0.3–0.5 mg DNA/ml resin.

The present invention provides an approach for the therapeutic treatment of SLE, based on hemoperfusion of the SLE patient through a column of the carbonized resin DNA immunoadsorbent. Blood is bled from an artery of a patient, pumped through the resin column to remove disease-causing substances, and returned to the patient's body through a vein usually for 2–3 hours. The hemoperfusion has been found to be safe, simple, and inexpensive.

Below is a detailed description of the methodologies of the present invention:

1. Preparation of Carbonized Resin

The organic phase was prepared by mixing 5.0–7.5% w/w of styrene, 10.0–12.5% w/w of divinylbenzene, 7.5–10.0% w/w of acrylonitrile, and 50% w/w of toluene, with addition of 0.15–0.3% w/w of the benzoyl peroxide initiator. After complete dissolution, 25.0% w/w liquid paraffin was added and mixed in thoroughly. The total amount of toluene and liquid paraffin was 3 times the total weight of the three monomers. A volume of 1–2% aqueous solution of polyvinyl alcohol twice the volume of the organic phase was placed in a 3L three-necked flask, and was warmed to 50° C. The organic phase was added with stirring and the temperature was increased to 80° C. for 3–5 hours. The temperature was then increased to 90–100° C. to distill the toluene. The globular polymer was boiled at 100° C. for 2 hours, filtered, and washed several times with hot distilled water. After drying in a 50° C. oven, the resin was washed or warm-extracted with petroleum ether to remove liquid paraffin. The resultant resin was a tri-component macroporous resin. Standard sieves were used to select the 0.45–1.0 mm sized resin beads.

The resin was pre-heated to 100–300° C. in a tubular resistance oven for 8–10 hours. Under $N_2$, the temperature was further increased at 100° C./hour to 500–800° C. Stearn was passed into the resin to activate the resin for 0.5–1.0 hour, and then allowed to cool to room temperature. About 350 ml of carbonized 0.45–0.9 mm resin was obtained.

The resin obtained was boiled in 2 volumes of 5% HCl for 30 minutes, washed with double distilled water until neutral pH, then boiled in 2 volumes of 5% NaOH, and again washed with double distilled water until neutral pH, and dried at 50° C. Finally it was extracted with hot absolute ethanol for 24 hours, and dried.

2. Preparation of Carbonized Resin DNA Immunoadsorbent (a) Preparation of DNA solution: High purity calf thymus DNA was dissolved in 0.2 M Tris-HCl, pH 7.4 buffer solution at a concentration of 4 mg/ml. An equal volume of saturated blue tetrazolium aqueous solution was added, followed by an equal volume of absolute ethanol. The mixture was stirred or shakened until complete dissolution.

(b) Preparation of collodion: 5% collodion ether solution was diluted 7.4 fold with absolute ethanol.

(c) DNA immobilization: 19–20% v/v DNA solution was mixed with 21.4–22.9 v/v of collodion solution. With continuous stirring, 57.1–59.5% v/v of carbonized resin was added and the liquid would be absorbed quickly. The mixture was kept at 50–60° C. for 1–2 hours, with intermittent stirring. After vacuum drying at 50° C. for 2 hours, the resin was washed with high purity injectable grade water until the eluent was devoid of absorbance at 260 nm. The DNA immunoadsorbent resin was vacuum dried at 50° C. for several hours.

250 mi of the DNA immunoadsorbent resin was placed in a column, sealed and sterilized. The resin was soaked in sterile physiological saline for at least 30 minutes, and flushed with 3000 ml sterile saline prior to clinical use. Patient's femoral artery and cephalic vein were cannulated. 1–1.5 mg/kg of heparin was intravenously infused into the patient 10–20 minutes prior to hemoperfusion. The whole system was kept at 37° C. After hemoperfusion was started, the flow rate was gradually increased from an initial 50 ml/min to 200 ml/min. Blood samples were obtained from peripheral artery for determination of anti-DNA antibodies, immune complexes and other blood biochemical assessments.

The present invention employs novel technologies to synthesize a high quality DNA immunoadsorbent resin. A very large amount of porogen in the form of toluene and liquid paraffin (equivalent to three times the total monomers and crosslinker) was used. The amount of the initiator and the rate of rise of reaction temperature were strictly controlled in order to control the polymerization process. The toluene was also rapidly evaporated in order to attain a macroporous resin structure and therefore a high surface area to volume ratio. The pre-heating of the resin, the programmed heating, the carbonization temperature, and activation with water vapor were all critical factors that determine the final yield and the structure and function of the carbonized resin, as illustrated in the Examples below. The carbonized resin prepared by the present method has the proper pore size and surface area to volume ratio (pore diameter of 20–35 Å, and surface area of 800–1200 $m^2$/ml) to be suitable for the preparation of immobilized DNA immunoadsorbent, and to be compatible with blood. It causes little damage to blood cells and platelets. The results of clinical applications have confirmed the excellent biomaterial properties of the carbonized resin DNA immunoadsorbent.

The carbonized resin DNA immunoadsorbent described in the present invention has been clinically tested on more than 150 patients in 28 hospitals in 17 cities in China. The treatment was effective in 98% of the patients. The treatment not only extended patient life span, but also allowed patients to recover their health and work capability. Tables 1 and 2 show part of the clinical results on SLE patients. As shown in Table 1, hemoperfusion brought about decreases in blood anti-dsDNA and improvements in proteinuria, ESR and anti-nuclueus titer. All ten patients survived longer than 32 months. One died in the $38^{th}$ month, but the other 9 all recovered their work capability. Furthermore, as shown in Table 2, five of the patients were hemoperfused repeatedly. Blood biochemistry was improved and clinical symptoms were progressively reduced. After treatment with the immunoadsorbent, four patients have stopped taking any steroids for 9, 12, 24, and 24 months (by the end of 1996). Only one of them died of the syndrome after one year. This demonstrates that hemoperfusion through the DNA immunoadsorbent resin of the present invention not only curtails the SLE clinical symptoms, but also helps to improve the patients' immune function to allow sustained therapeutic effects, and makes recovery possible in some cases.

THE PREFERRED PRACTICE OF THE PRESENT INVENTION

EXAMPLE 1

Preparation of Carbonized Resin 45.0 g styrene, 60.0 g divinylbenzene, 45.0 g acrylonitrile, and 300.0 g of toluene were mixed, and 1.5 g of benzoyl peroxide was added. After dissolution, 160.0 g liquid paraffin was added and mixed in thoroughly. This mixture was added to 1150 ml 1% polyvinyl alcohol aqueous solution placed in a 3000 ml three-necked flask at 50° C. After mixing, the temperature was increased to 80° C. over 1 hour, and reaction was carried out for 5 hours. The temperature was then increased to higher above 90° C. to distill off the toluene for about 1 hour, until the distillation was complete. The globular polymer was boiled at 100° C. for 2 hours to allow further polymerization and hardening, filtered and washed several times with hot distilled water to remove polyvinyl alcohol. After drying in a 50° C. oven, the resin was washed with petroleum ether (60–90° C.) to remove paraffin. The resultant resin was sieved to yield about 400 ml resin of 0.45–1.0 mm beads.

1000 ml of the resin obtained was placed in a tubular resistance oven and preheated at 200° C. for 10 hours. Under $N_2$, the temperature was then rapidly increased at 100° C./hour to 800° C. Water vapor was introduced to activate the resin for 1 hour at this high temperature. About 350 ml of carbonized resin beads of 0.45–0.9 mm with a surface area of 1000–12000 $m^2$/g, and average pore diameter of 20–35 Å was obtained after cooling to room temperature.

Preparation of the Carbonized Resin DNA Immunoadsorbent 250 ml of the carbonized resin obtained was boiled with 2 volumes of 5% HCl for 30 minutes, washed with double distilled water until neutral pH, then boiled in 2 volumes of 5% NaOH, and again washed with double distilled water until neutral pH. After oven drying at 50° C., it was refluxed with absolute ethanol for 24 hours, and dried for use.

In the following procedure, all solutions employed were prepared with injectable grade water under aseptic conditions, and purified DNA was used in order to ensure that the resin product was free of pyrogens.

80 ml of calf thymus DNA solution (made by dissolving 4 mg/ml DNA in 0.2M Tris-HCl, pH 7.4, adding sequentially equal volume of saturated aqueous blue tetrazolium solution and absolute ethanol, and stirring until all thread-like materials were dissolved) was placed in a 1000 ml beaker. 90 ml of collodion solution (made by diluting 55 ml of 5% collodion ether solution with 350 ml absolute ethanol) was added. With rapid stirring, 250 ml of carbonized resin was added and the liquid would be absorbed quickly. The mixture was kept on a 50–60° C. water bath for 2 hours, with intermittent stirring until the solvent was completely evaporated. The resin was vacuum dried at 50° C. for 2 hours, washed several times with injectible grade water, placed in a column, washed with injectible grade water until the eluent was devoid of absorbance at 260 nm. The DNA immunoadsorbent resin was water washed several times more, and vacuum dried at 50° C. The DNA content was 0.38 mg/ml resin. The product was tested to ensure absence of pyrogen by rabbit pyrogen test.

EXAMPLE 2

When the procedure of Example 1 above was carried out using a carbonization temperature of only 580° C. in the tubular resistance oven, while keeping all other conditions the same, the surface area of the resultant resin was reduced to about 100 m/g. The DNA content of the final immunoadsorbent resin was correspondingly greatly reduced.

EXAMPLE 3

When the procedure of Example 1 above was carried out using only 0.5 hour of activation of the resin by water vapor, while keeping all other conditions the same, the surface area of the resultant resin was about 800–1000 m²/g. The DNA content of the final immunoadsorbent resin would also be reduced.

EXAMPLE 4

When the procedure of Example 1 above was carried out by immediately heating up the resin to 800° C. under $N_2$, without preheating at 200° C. for 10 hours, while keeping all other conditions the same, the yield of carbonized resin was less than 200 ml, even though the same amounts of starting materials were used. Therefore the preheating treatment of the resin greatly increased the yield of carbonized resin.

EXAMPLE 5

When the procedure of Example 1 above was carried out employing instead 87.5 ml of calf thymus DNA solution, 100 ml of collodion solution, and 250 ml of carbonized resin, while keeping all other conditions the same, the DNA immobilized on the resin was increased slightly to 0.42 mg/ml resin.

EXAMPLE 6

When the procedure of Example 1 above was carried out using double distilled water instead of injectable grade water in the washing steps, while keeping all other conditions the same, pyrogenic substances were detected in the carbonized resin DNA immunosorbent by the rabbit pyrogen test. It is therefore important to use injectible grade water in washing the resin in order to avoid contamination by pyrogens.

INDUSTRIAL APPLICATION

The present invention has yielded an improved DNA immobilization method that increases the immobilization efficiency, enhances immunoadsorbent function, and makes possible the avoidance and removal of pyrogen. This results in a DNA immunoadsorbent resin with excellent capability and suited to clinical applications. Furthermore, on account of the ready availability of the raw materials employed, and the straightforward immobilization conditions, the present invention also substantially reduces the production costs for the DNA immunoadsorbent.

TABLE 1

Summary of Ten SLE Cases (followed up to February 1998)

| | Particulars | | | | | | Clinical Chemistry (Before/1 Week After Hemoperfusion | | | | | |
|---|---|---|---|---|---|---|---|---|---|---|---|---|
| | | | | | | | Serum | | | | | |
| No. | Gender | Age | Date of SLE Diagnosis | Treatment Date | Proteinuria | ESR | immunoglobulin (g/L) | Anti-nucleus titer | Plasma C3 | Anti-dsDNA | No. of Hemoperfusion | Outcome (Survival/ Daily Life) |
| 1 | F | 23 | Jan 1992 | Jun 1994 | ++/− | 42/13 | 13.6/240 | 1280/1.23 | 0.42/16.2 | 34.8/ | 2 | Survived 44 months Back to work |
| 2 | F | 34 | Jul 1993 | Jul 1994 | +++/+ | 38/12 | 18.6/14.3 | 800/80 | 0.31/0.81 | 36.5/16.0 | 2 | Survived 38 months Died of hemolysis |
| 3 | F | 31 | Apr 1994 | Oct 1994 | ++/− | 58/14 | 19.3/14.1 | 1040/160 | 0.40/1.22 | 34.3/16.3 | 2 | Survived 40 months House work |
| 4 | F | 29 | Nov 1992 | Nov 1994 | ++/− | 40/16 | 14.4/ | 160/ | 0.51/1.31 | 18.0/ | 2 | Survived 39 months House work |
| 5 | M | 31 | Jul 1994 | Mar 1995 | ++/− | 55/18 | 21.3/12.6 | 880/160 | 0.43/1.24 | 17.5/ | 2 | Survived 35 months Back to work |
| 6 | M | 32 | Mar 1992 | Mar 1995 | +++/+ | 43/16 | 19.3/11.4 | 1280/240 | 0.32/1.67 | 28.5/14.1 | 2 | Survived 35 months House work |
| 7 | F | 33 | Nov 1994 | Mar 1995 | +/− | 65/16 | 12.5/ | 1280/240 | 0.81/ | 33.4/14.5 | 1 | Survived 35 months Back to work |

TABLE 1-continued

Summary of Ten SLE Cases (followed up to February 1998)

| | | | Particulars | | | | Clinical Chemistry (Before/1 Week After Hemoperfusion) | | | | | |
|---|---|---|---|---|---|---|---|---|---|---|---|---|
| | | | | | | | Serum | | | | | |
| No. | Gender | Age | Date of SLE Diagnosis | Treatment Date | Proteinuria | ESR | immuno-globulin (g/L) | Anti-nucleus titer | Plasma C3 | Anti-dsDNA | No. of Hemo-perfusion | Outcome (Survival/ Daily Life) |
| 8 | F | 41 | Apr 1991 | Apr 1995 | +++/− | 78/18 | 18.6/10.5 | 80/ | 0.83/ | 31.1/16.6 | 2 | Survived 34 months Self managed daily life |
| 9 | M | 24 | Mar 1995 | May 1995 | ++/− | 66/14 | 20.2/13.2 | 1200/160 | 0.54/1.21 | 33.8/15.5 | 2 | Survived 33 months Back to heavy duty work |
| 10 | F | 26 | Jan 1995 | Jun 1995 | +/− | 52/16 | 19.2/12.7 | 1040/80 | 0.86/ | 36.8/15.7 | 1 | Survived 32 months Back to catering service work |

TABLE 2

Summary of Five SLE Cases (followed up to the end of 1996)

| | | | | | | | | Kidney function | | | | |
|---|---|---|---|---|---|---|---|---|---|---|---|---|
| | | | | | Antibody | | | Protein-uria | Blood urea nitrogen | Plasma creatinine | ESR | |
| No | Gender | Age | Hemo-perfusion | ds-DNA | anti-SM | ANA | | g/24 hr | mmol/L | μmol/L | mm/hr | Outcome |
| 1 | F | 41 | Before | + | ± | 1280 | | 2.0 | 9.5 | 320 | — | Followed for 9 months |
| | | | 1st | ± | ± | 640 | | 1.8 | 7.8 | 288 | — | No steroid treatment |
| | | | 2nd | ± | − | 320 | | 1.7 | Normal | Normal | — | Clinically stable |
| | | | 3rd | − | − | 320 | | 1.5 | Normal | Normal | — | |
| 2 | F | 35 | Before | − | + | 1280 | | | | | 30 | Followed for 1 year |
| | | | 1st | − | + | 320 | | | | | 25 | No steroid treatment |
| | | | 2nd | − | − | 160 | | | | | 20 | Clinically stable |
| | | | 3rd | − | − | 160 | | | | | — | |
| 3 | F | 38 | Before | + | + | 320 | | 3.5 | 25 | 450 | 80 | No steroid treatment |
| | | | 1st | − | ± | 160 | | 3.0 | 16 | 350 | — | Died of complications |
| | | | 2nd | − | ± | 80 | | 2.5 | 10 | 250 | 50 | 1 year after hemoperfusion |
| | | | 3rd | − | − | 40 | | 2.6 | 18 | 350 | 30 | |
| 4 | F | 34 | Before | + | + | 640 | | 0.26 | 4.1 | 75 | 28 | Followed for 2 years |
| | | | 1st | − | + | 640 | | Normal | Normal | Normal | — | No steroid treatment |
| | | | 2nd | + | + | 640 | | Normal | Normal | Normal | 28 | Normal antibodies levels |
| | | | 3rd | − | − | 320 | | Normal | Normal | Normal | 18 | |
| 5 | F | 28 | Before | + | + | 320 | | — | — | — | 94 | Followed for 2 years |
| | | | 1st | + | + | 320 | | Normal | Normal | Normal | 85 | No steroid treatment |
| | | | 2nd | − | + | 320 | | Normal | Normal | Normal | 45 | Clinically stable Worked as farmer |

We claim:

1. A method for preparing a carbonized resin DNA immunoadsorbent by immobilizing an effective amount of DNA on a carbonized resin as a carrier, in which the DNA content is 0.3–0.5 mg/ml resin, where the distinctive preparation steps are:

(c) Preparation of carbonized resin

Styrene and acrylonitrile are used as monomers, divinylbenzene as crosslinker, toluene and liquid paraffin equal to 3 times the weight of combined monomers as porogen, benzoyl peroxide as initiator, 1–2% aqueous solution of polyvinyl alcohol as dispersing medium. Polymerization is carried out in suspension at 80° C. for 5 hours. Toluene is distilled off at 96° C. The globular resin is boiled at 100° C. for 2–3 hours for further polymerization and hardening, washed with hot water, and then dried by heating at 50° C. Petroleum ether is used to remove paraffin from the resin. The resultant resin is a tri-component macroporous resin. The resin is heated under protection with inert gas to 100–300° C. in an oven for 8–10 hours, raised to 500–800° C., and treated with water vapor to activate the resin for 0.5–1.0 hour. The carbonized resin is obtained after cooling.

(d) Preparation of the carbonized resin DNA immunoadsorbent

Calf thymus DNA solution is mixed with collodion ether solution. Under vigorous stirring, the carbonized resin is added to quickly absorb the liquid. The reaction mixture is washed with intermittent stirring in a 50–60° C. water bath for 2 hours until the solvent is totally evaporated. The resin is vacuum dried at 50° C. for 2 hours, packed into a column, and washed with water until the eluent is devoid of absorbance at 260 nm. The resin is further washed again and vacuum dried at 50° C.

2. A carbonized resin DNA immunoadsorbent as claimed in claim 1 wherein the amounts of materials employed are:

(a) Preparation of carbonized resin: the organic phase comprises monomers of styrene (5.0–7.5% w/w) and acrylonitrile (7.5–10.0% w/w), divinylbenzene crosslinker (10.0–12.5% w/w), toluene (50.0% w/w), liquid paraffin (25.0% w/w), and benzoyl peroxide initiator (0.15–0.3% w/w). The amount of benzoyl peroxide employed is 0.5–1.0% the amount of styrene plus divinylbenzene. The water phase is 1–2% polyvinyl alcohol. The organic phase:water phase weight ratio is 1:2;

(b) Preparation of the carbonized resin DNA immunoadsorbent: amount of carbonized resin used is 57.1–59.5% v/v, DNA solution 19–20% v/v, collodion ether solution 21.4–22.9% v/v, DNA concentration 1.33 mg/ml, collodion concentration 0.68%.

* * * * *